United States Patent [19]

McGee et al.

[11] 3,945,044
[45] Mar. 23, 1976

[54] GOGGLE AND ACCESSORIES THEREFOR
[75] Inventors: Charles D. McGee, Ketchum; Charles S. French, Sun Valley, both of Idaho
[73] Assignee: Scott USA, Sun Valley, Idaho
[22] Filed: Mar. 7, 1974
[21] Appl. No.: 449,096

[52] U.S. Cl. ................................................. 2/14 H
[51] Int. Cl.² ............................................ A61F 9/02
[58] Field of Search ......... 2/14 N, 14 K, 14 C, 14 J, 2/14 B, 14 H, 14 M, 14 R, 14 Q, 13, 9, 8; 351/47

[56] References Cited
UNITED STATES PATENTS

| | | | |
|---|---|---|---|
| 1,795,866 | 3/1931 | King | 2/8 |
| 2,511,329 | 6/1950 | Craig | 351/47 |
| 2,618,782 | 11/1952 | Christensen et al. | 2/14 K |
| 2,864,088 | 12/1958 | Gongoll | 2/14 H |
| 2,907,041 | 10/1959 | Finn | 351/47 X |
| 3,031,675 | 5/1962 | Dubach | 2/14 Q |
| 3,033,359 | 5/1962 | Mercer | 351/47 |
| 3,233,956 | 2/1966 | De Angelis | 2/14 M |
| 3,298,031 | 1/1967 | Morgan | 2/14 B X |
| 3,368,221 | 2/1968 | Anderson | 2/14 N |
| 3,395,406 | 8/1968 | Smith | 2/14 N |
| 3,705,760 | 12/1972 | Langendorfer | 2/14 C |

Primary Examiner—Werner H. Schroeder
Assistant Examiner—Peter Nerbun
Attorney, Agent, or Firm—Wegner, Stellman, McCord, Wiles & Wood

[57] ABSTRACT

A goggle frame includes air vents spaced along its periphery and covered with a fibrous lining to vent the goggle interior while preventing entry of foreign matter. A detachable partial-face shield has snap-in posts which mate with apertures spaced along a bottom rim of the goggle frame. When the shield is attached to the rim, a shield nose section rests on a nose bridge of the frame, and shield side sections curve behind adjacent air vents in the frame to force frontal air therethrough. A main lens has locking projections received in a peripheral groove around the frame. One or more auxiliary lenses have edge regions received in the same peripheral groove, each auxiliary lens having an offset tab to allow a wearer to detach the auxiliary lens while the goggle is being worn.

18 Claims, 5 Drawing Figures

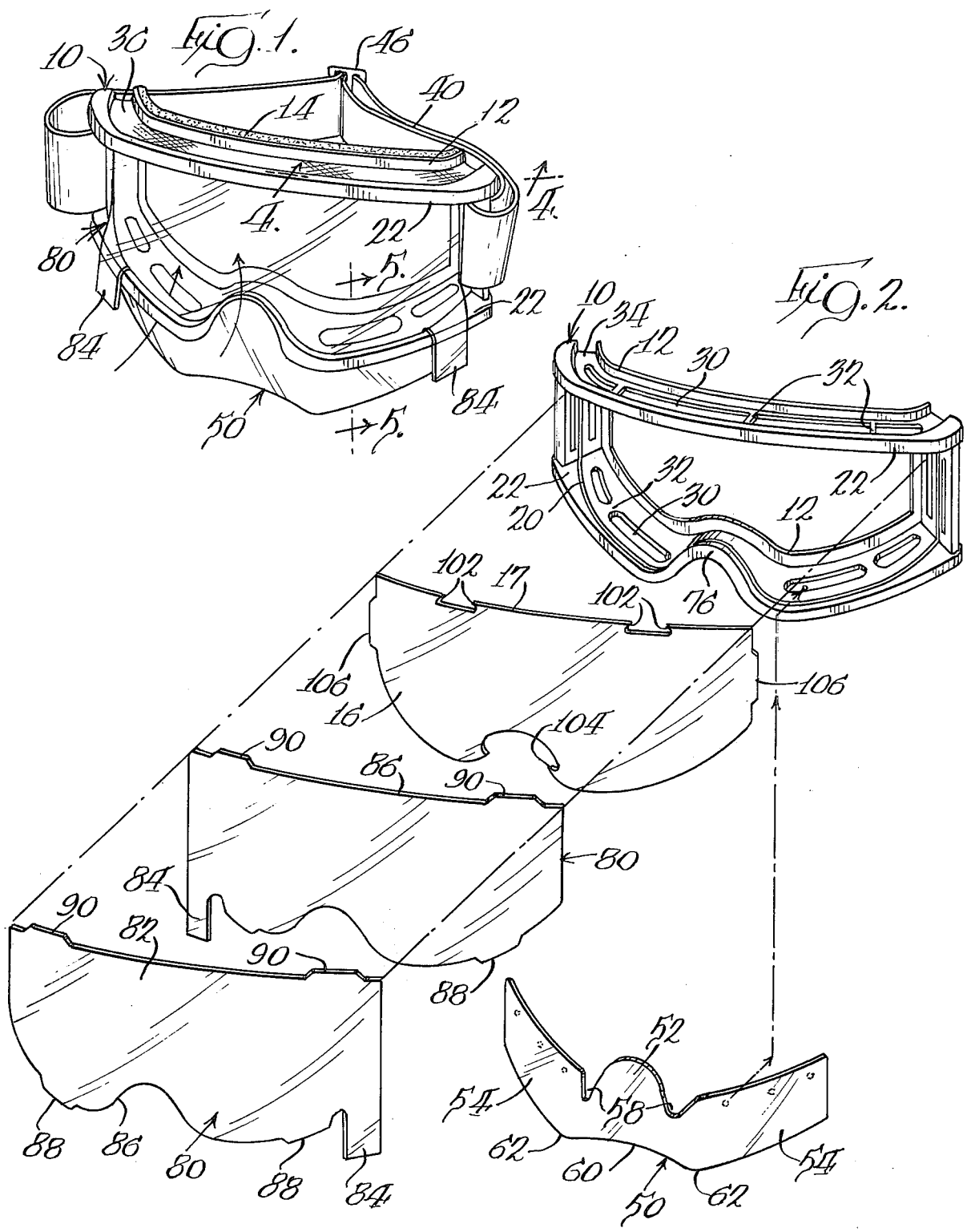

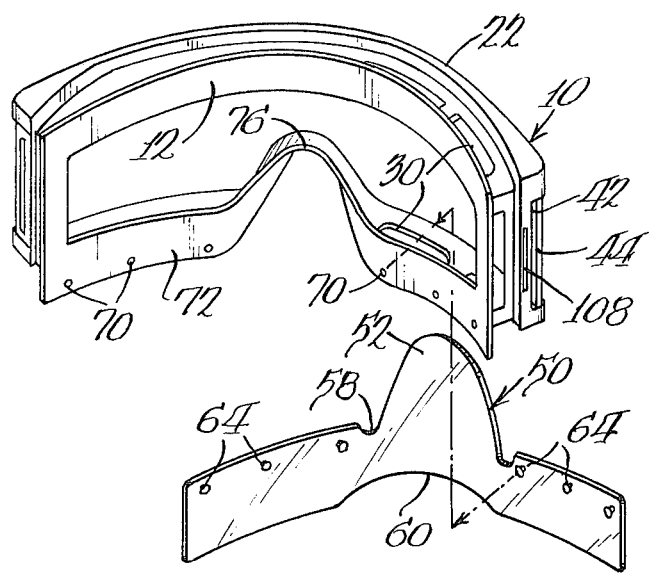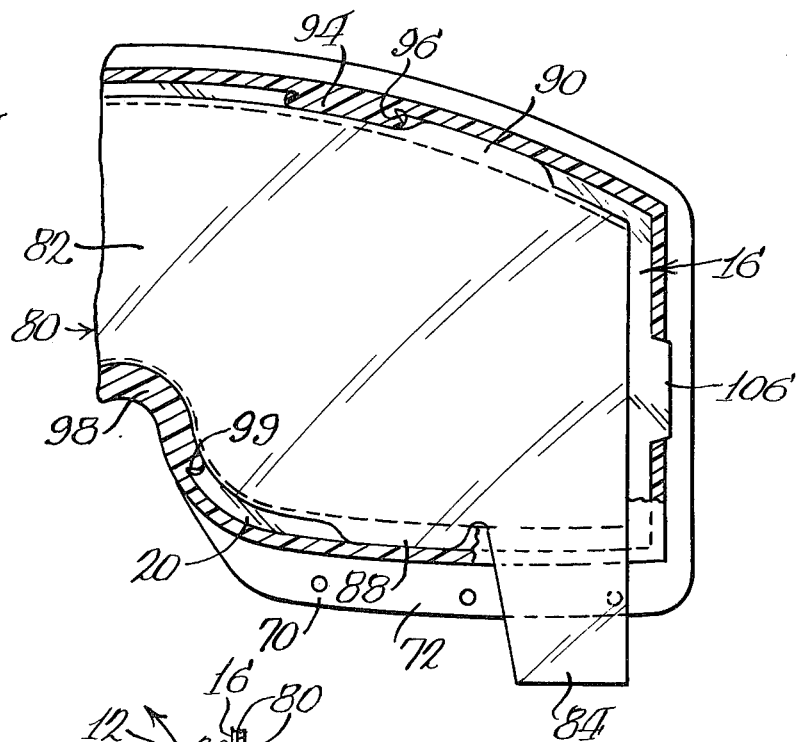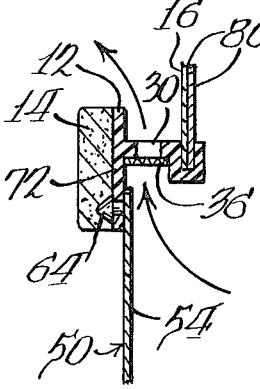

GOGGLE AND ACCESSORIES THEREFOR

BACKGROUND OF THE INVENTION

This invention relates to a goggle having accessories such as a face-protecting shield and a detachable auxiliary lens.

Goggles used for motorcycle racing and other activities where foreign matter is directed toward the face of a wearer often include a detachable face shield, and a disposable or tear-off lens. Many detachable face shields include snap fasteners which are received in male connections on the goggle frame to allow the shield to be detached, when desired. An example of such a detachable face shield, formed of self-supporting transparent plastic material, is shown in U.S. Pat. No. 3,298,031 to Morgan. Detachable face shields have also been formed of fabric with metal screening protecting open breathing regions.

To prevent fogging and allow a slow exchange of interior air, it has been well known to incorporate air-flow ventilation means in a goggle frame. Such ventilation means may take the form of apertures which directly vent to atmosphere, or serpentine or covered passageways, which directly vent to atmosphere but block direct entry of foreign matter, or larger vent apertures covered by a fibrous or foam material or liner. Some prior detachable face shields have blocked the air-flow ventilation means, or have allowed moisture-laden air from the nose or mouth of the wearer to circulate toward the air-flow ventilation means and create a fogging condition. Detachable face shields formed of fabric have been unsatisfactory in that fabric does not distribute stress over the shield, and allows flying gravel or the like to penetrate at its point of impact.

When the goggle is to be used in an environment in which the lens may become muddy, scratched, or otherwise damaged, auxiliary disposable lenses (commonly called tear-off lenses) are attached to the front of the goggle frame. Extra snaps and posts on the goggle frame project forwardly and allow an auxiliary or disposable lens to be attached in spaced relation to the goggle frame. Some auxiliary lenses have had side tabs extending outwardly beyond the goggle frame to allow the weater to grasp the tab and tear off the auxiliary lens while the goggle is being worn. Any tear-off auxiliary lens must be easily detached using one hand and minimum effort, without jarring or displacing the goggle or the main lens.

Prior goggles having tear-off lenses have been undesirable in several respects. The auxiliary lens is attached to the goggle frame by posts and other protrusions on the goggle frame, and the auxiliary lens is oversized with protruding left and right tabs to allow the wearer to grasp the lens. All of these features create gaps which allow dirt, dust, mud and the like to enter the space between the auxiliary lens and the main lens. While some goggles have allowed attachment of more than one auxiliary lens, the tabs therefore overlie each other and care must be used in separating and grasping the outermost tab. In addition to being impractical during motorcycle racing or the like conditions, the additional tear-off lenses are liable to all become detached at the same time. To overcome dirt entering between the lenses, goggles of a different type have used detachable auxiliary lenses which lie somewhat flat against the main lens, such as shown in U.S. Pat. No. 2,409,286 to Joyce, but such auxiliary lenses are internally mounted and cannot be adapted to the tear-off type.

SUMMARY OF THE INVENTION

In accordance with the present invention, the above noted problems with prior goggles having face shields and detachable tear-off lenses have been overcome. A partial-face shield of simple construction carries snap-in posts which are received in spaced apertures along a lower rim of the goggle frame. The resulting detachable connection curves the shield backward and behind air-flow ventilation means located in the bottom section of the frame to force frontal air through the bottom air-flow ventilation means, and prevent moisture-laden air adjacent the wearer's face from entering the goggle interior. The lower rim carries a padding which cushions the contact with the wearer's face, and also prevents contact with the snap-in posts.

One or more tear-off auxiliary lenses are carried within the same peripheral groove which mounts the main lens to the goggle frame. The peripheral groove sealingly engages the auxiliary lens and prevents foreign matter from entering between the auxiliary lens and the main lens. The auxiliary lens has a different edge configuration than the main lens, and includes a single sided extending tab to allow easy detachment of the auxiliary lens without jarring or displacing the main lens. Two auxiliary lenses may be carried by the goggle frame, each having a tab offset with respect to the other to allow quick detachment of only one auxiliary lens at a time.

Both the face shield and the auxiliary lenses are formed of simple, economical components, and can be detached readily from the goggle frame to allow the goggle to be used by itself. When the accessories are detached, the goggle frame has no posts or other undesirable projections.

One object of the present invention is the provision of a goggle having an improved extending shield which cooperates with air-flow ventilation means in a goggle frame to prevent fogging, and/or has novel connector means for easy detachment from the goggle frame.

Another object of the present invention is the provision of a goggle having an improved tear-off auxiliary lens which sealingly engages a goggle frame to prevent entry of foreign matter, and/or has improved connector means for detaching the auxiliary lens while the goggle is being worn.

Other objects and features of the invention will be apparent from the following description and from the drawings. While an illustrative embodiment of the invention is shown in the drawings and will be described in detail herein, the invention is susceptible of embodiment in many different forms and it should be understood that the present disclosure is to be considered as an exemplification of the principles of the invention and is not intended to limit the invention to the embodiment illustrated.

BRIEF DESCRIPTION OF THE DRAWINGS

FIG. 1 is a perspective view of the novel goggle with an attached face shield and two tear-off auxiliary lenses;

FIG. 2 is an exploded view showing the goggle frame, the main lens, two tear-off auxiliary lenses, and the detachable shield;

FIG. 3 is a rear perspective view of the goggle frame and detachable shield;

FIG. 4 is a cross-sectional view taken along lines 4—4 of FIG. 1; and

FIG. 5 is a fragmentary cross-sectional view taken along lines 5—5 of FIG. 1.

DESCRIPTION OF THE PREFERRED EMBODIMENT

Turning to the drawings, the novel goggle with accessories (shown attached in FIG. 1) includes a goggle frame 10 which may be molded of one piece from a resilient flexible material such as a soft plastic or soft rubber. A face contacting flange or rim 12 is lined with a padding or cushion 14 of sponge-type material to seal the frame against the user's face. A main lens 16 of transparent material, which may be colored if desired, has a peripheral edge 17 which is received within a peripheral groove 20 formed interiorly around a front section 22 of the frame 10. Main lens 16 may be flat and bent to an arcuate configuration which fits the frame, or may be curved and could, if desired, form a part of the structural support to maintain the shape of the goggle.

Goggle frame 10 has a plurality of air-flow ventilation means spaced around an intermediate section of the rim 12. Illustratively, the air-flow ventilation means comprises a plurality of large vent openings 30 formed by ribs 32 which join the rim 12 to the forward section 22. On the exterior side, the ribs define with the rim 12 and forward section 22 a channel 34 for a fibrous or foam-type lining 36 which covers the openings to allow a slow exchange of atmosphere between the goggle exterior and the generally confined interior space located between the main lens 16 and the wearer's face. Other conventional air-flow ventilation means, however, may be utilized in place of the illustrated vent apertures covered by a fibrous strip.

To secure the goggle to the wearer's head, an elastic headband or strap 40 has folded, stitched ends which are received in slots 42 formed by posts 44 spaced from the remainder of the front frame section 22. A slide buckle 46 allows adjustment of the length of the elastic strap 40. The goggle structure described above is well known, and various modifications may be made thereto as desired.

In accordance with one aspect of the present invention, a partial-face shield 50 is detachable with a lower portion of the goggle frame 10. The shield 50 may be formed of a generally hard plastic material, opaque or translucent, having sufficient resiliency to be self-supporting, and molded to one piece. The shield 50 includes a nose section 52 and integral side sections 54 extending from the nose section. A pair of notches 58 are formed between the sides of the nose section 52, and the upper edges of the side sections 54. The base of the guard has a central arcuate edge 60 which curves towards a pair of lowermost protuberances 62 which curve slightly upward to form the bottom edge of the side sections 54. On the rear plane or back of the shield 52, along the upper edges of only the sides 54, are a plurality of snap-in posts 64.

To detachably connect the partial-face shield 50 to the goggle frame 10, the face contacting rim 12 extends downwardly below the bottom edge of the front frame section 22 (see FIG. 4), and carries in the extension or base 72 a plurality of apertures or holes 70. To attach shield 50 to the goggle frame 10, the nose section 52 is placed in front of a central nose bridge 76, formed by a central depression in the goggle frame. The shield side sections 54 are then bent rearwardly and the snap-in posts 64 are urged through the receiving holes 70 in the lower rim base 72.

As seen in FIG. 5, the snap-in posts 64 have a head larger than a neck portion, with the head also being of larger diameter than the diameter of the receiving holes 70. Since the entire goggle frame 10 is formed of a resilient plastic, the hole diameter will expand as the head portion of the post 64 is urged through the hole, and then retract around the neck portion so as to form a detachable connector. Although the above construction is preferred in that it allows the entire shield 50 to be formed of rigid plastic, it will be understood that the snap-in posts 64 could be formed of a resilient material, and the rim base 72 could be formed of a more rigid material.

When the posts 64 are snapped in place, the cushion or padding 14 prevents the posts 64 from coming in contact with the wearer's face. The padding 14 may be cemented or otherwise secured to the rim 12, and should have a sufficient width to cover the receiving holes 70 and a sufficient thickness, greater than the head of the posts 64, so as to prevent the wearer's face from coming in contact with the posts. It will be understood that the male portion of the connectors could be formed on the goggle frame, and the female portion could be formed in the shield 50, although such construction is not preferred since it would leave a series of protruding posts on the goggle frame when the shield was not in place.

Shield notches 58 allow the side sections 54 to be tucked under and bent rearwardly to attach to the rim base 72 while the nose section 52 rests against and covers the nose bridge 76 of the goggle frame. As a result of this construction, the side sections 54 are located behind the air-flow ventilation means formed in the bottom section of the goggle frame. As seen in FIGS. 1 and 5, this allows frontal air, illustrated by the arrows, to strike the shield and be deflected upwardly through the foam liner 36 and vent holes 30 into the interior of the goggle. Frontal air flowing toward the center of the shield is deflected by the nose section upwardly and across the exterior face of the goggle. Since air near the center may carry additional moisture, because it is in the vicinity of the nose and mouth regions of the wearer's face, it is deflected and flows on the outside of the goggle.

When attached by the snap connectors, the shield 50 is self-supporting and is spaced away from the wearer's face a sufficient distance to fit over a football or joffa-type mouth protector. The width or span of the goggle frame 10 is preferably less than the opening between conventional racing helmets, so as to allow the use of the goggle within the racing helmet. It should be noted that the detachable shield 50 is located over only the frontal section of the goggle frame, and does not extend around or to the side of the goggle frame, for ease of using the shield within the racing helmet or similar headgear protector.

Also in accordance with the present invention, one or more tear-off or detachable auxiliary lenses 80 may be temporarily attached to the goggle frame 10, and detached for disposal when mud or other foreign material covers the lenses. Each auxiliary lens 80 may be molded of transparent plastic and has a flat, bendable body 82 and one extending tab 84. Around a peripheral edge 86 of the transparent body, a pair of bottom ears 88 and a pair of top ears 90 protrude for reasons to be explained. A single die-cut blank may form both auxiliary lenses by flipping one die-cut blank by 180° so as to cause the tab therefore to extend from the opposite side of the body.

Goggle frame 10 includes means spaced around the periphery of the frame for engaging at least a portion of the edge surface 86 of the auxiliary lens 80 to form a detachable seal between the disposable lens 80 and the frame 10. While the detachable seal means may take various forms including a separate peripheral groove, herein it is formed by the same peripheral groove 20 as mounts the main lens 16. As seen in FIG. 4, the peripheral groove 20 is formed by a two-depth channel with the deeper channel being formed around the majority of the periphery of the frame, and the lesser channel formed by upper ridges 94, which have an undercut 96 to the deeper channel, and a nose ridge 98, having an undercut 99.

The peripheral edge 17 of the main lens carries pairs of pointed protrusions 102 which mate with the projection receiving recesses or undercuts 96. The edge 17 includes a pair of pointed protrusions 104 which mate with the nose undercuts 99. Finally, the edge 17 includes a pair of ears 106 which extend into a pair of side slots 108 which may be formed through the entire frame 10. The main lens 16 may be changed to a different color, or replaced, by manipulation of the flexible frame 10 so as to detach the pointed protuberances from the undercuts, and to detach the ears from the side slots. Once the main lens 16 is properly positioned within the peripheral groove 20, the pointed protuberances and ears lock the main lens in place, and prevent its detachment except when the goggle is off the head of the wearer and the frame is properly manipulated.

The peripheral edge 86 of the auxiliary lens 80 is different than the peripheral edge 17 of the main lens 16, and is designed for easy release from the groove 20. The majority of the peripheral edge 86 is just barely received within the peripheral slot 20, as seen in FIG. 4. The top ears 90 and bottom ears 88 of the auxiliary lens correspond in height with the height of corresponding locations along the main lens 16 when the lenses 16 and 80 are superimposed. The auxiliary lens 80 also lacks the ears 106 of the main lens, which ears extend into the side slots 108. Due to this construction, the wearer may grasp one of the tabs 84 and yank the auxiliary lens 80 outwardly and out of attachment with the groove 20. Because the auxiliary lens 80 and the main lens 16 are substantially in sealing engagement with the goggle frame and with each other, it is very difficult for dirt, dust, mud or the like to enter between the lenses.

The second tear-off lens is flipped and inserted within the groove so that its tab 84 does not overlie, and is substantially spaced from, the first mentioned tab 84. Thus, a pair of tear-off auxiliary lenses 80 may be inserted in the goggle frame at one time, each having a separate left or right tab which allows the wearer to easily grasp the correct tab, even with a gloved hand, and yank out the desired auxiliary lens with a simple hand motion and without displacing the main lens 16. Desirably, the tabs are located in front of the shield side sections 54, since this shield curves rearward and thereby creates the maximum finger space between the shield and the tabs when the tabs are located as illustrated.

It will be appreciated that the tear-off auxiliary lenses or the detachable shield may be separately incorporated in a goggle frame. Also, the detachable shield may be permanently affixed to the bottom of the goggle frame, if so desired. While the main lens 16 has been illustrated as being a single lens, a sealed double thermal lens could be substituted therefore. Other modifications and changes may be made following the above teachings.

We claim:
1. A goggle comprising:
a detachable main lens having a peripheral edge surface;
a disposable tear-off lens having a peripheral edge surface and an extending tab;
a flexible frame having means for detachably mounting the edge surface of the main lens to allow release of the main lens by manipulation of the flexible frame, the flexible frame including a peripheral groove extending around the periphery of the frame with at least portions of the edge surface of the disposable tear-off lens extending into the peripheral groove to form a detachable seal therewith,
the tab of the disposable tear-off lens extending beyond the frame when the edge surface of the disposable tear-off lens is engaged in the peripheral groove to allow a wearer to grasp the tab and yank outwardly to disengage the seal and release the disposable tear-off lens from the flexible frame without releasing the detachable main lens while the goggle is being worn.

2. The goggle of claim 1 wherein the frame has a face contacting rim and a lens mounting section which supports the main lens in spaced relation to a wearer's face and defines a generally confined interior space, the frame includes air-flow ventilation means located between the rim and the lens mounting section to vent the interior space to external air, the peripheral groove extending around the inner periphery of the lens mounting section and in front of the main lens with the edge surface of the disposable tear-off lens extending into the peripheral groove to thereby detachably seal the disposable tear-off lens in front of the main lens.

3. The goggle of claim 1 including a second disposable tear-off lens having a second peripheral edge surface and a second extending tab, the edge surface of the first named disposable tear-off lens extending into the peripheral groove with the tab of the first named disposable tear-off lens extending beyond the frame at one side thereof and the second edge surface extending into the peripheral groove with the second tab of the second disposable tear-off lens extending beyond the frame at an opposite side to prevent the tabs from being located adjacent each other.

4. The goggle of claim 3 wherein the first named disposable tear-off lens and the second disposable tear-off lens are formed of identical shapes, one of the disposable tear-off lenses being flipped 180° when its edge surface extends into the peripheral groove to thereby space the tabs at opposite sides of the goggle frame.

5. The goggle of claim 1 wherein the frame includes a face contacting rim, a lens engaging section located at the front of the frame, and an intermediate section for spacing the lens engaging section from the rim, a shield extending from the frame for protecting a portion of the wearer's face which is not covered by the frame and lenses, at least a recessed portion of the shield being attached to the rim, and the peripheral groove being located in the lens engaging section to locate the tab of the disposable tear-off lens in front of the lens engaging section of the frame and in front of the recessed shield portion which is attached to the rim to thereby create a space corresponding to the intermediate section to allow easy grasping of the tab when the tear-off lens is to be detached.

6. The goggle of claim 1 wherein the edge surface of the disposable tear-off lens includes a plurality of ears which extend fully into the peripheral groove of the frame with the remaining extent of the edge surface having dimensions to extend only partially into the peripheral groove to allow easy detachment from the frame when the tab is yanked outwardly.

7. A goggle comprising:
a detachable main lens having a first peripheral edge surface;
a detachable auxiliary lens having a second peripheral edge surface different in shape than the first peripheral edge surface and an extending tab;
a frame for maintaining the main lens in spaced relation to a wearer's face and the auxiliary lens abutting against the main lens until detached from the frame, including
a peripheral groove extending around the inner periphery of the frame, at least portions of the edge surfaces of the detachable main lens and the detachable auxiliary lens extending into the same peripheral groove by different amounts with the peripheral groove engaging to a greater extent the first peripheral edge surface
the tab of the auxiliary lens extending from the frame when the edge surface of the auxiliary lens is engaged by the peripheral groove to allow a wearer to grasp the tab and disengage the detachable auxiliary lens from the frame while the goggle is being worn without disengaging the detachable main lens.

8. The goggle of claim 7 wherein the peripheral edge surface of the main lens includes a plurality of locking projections which mate with lock receiving recesses in the peripheral groove, and the different shape peripheral edge surface of the auxiliary lens lacks the locking projections.

9. The goggle of claim 7 wherein the peripheral edge surface of the auxiliary lens includes a plurality of extending ears which extend into the peripheral groove a distance corresponding to the peripheral edge surface of the main lens with the remaining extent of the edge surface of the auxiliary lens extending only partially into the peripheral groove to allow easy detachment from the frame.

10. A goggle comprising:
a lens,
a frame having a top section, side sections and a bottom section which includes a central nose bridge for supporting the lens in spaced relation to a wearer's face, only the bottom section of the frame includes a first plurality of frame connectors spaced on one side and a second plurality of frame connectors spaced on the opposite side of the central nose bridge,
a detachable shield with a nose section devoid of any connector and a pair of side sections extending from the shield nose section towards but not around the sides of the frame when attached thereto and formed of a self-supporting material for protecting a lower portion of the wearer's face, one of the shield side sections containing a first plurality of shield connectors for detachable mating engagement with the first plurality of frame connectors and the other of the shield side sections containing a second plurality of shield connectors for a detachable mating engagement with the second plurality of frame connectors to attach the shield in a self-supporting relationship to the bottom section of the frame with the shield nose section extending vertically adjacent and overlapping the central nose bridge without attachment thereto to thereby deflect some of the frontal air up over the exterior of the lens.

11. The goggle of claim 10 wherein at least the bottom section of the frame includes air-flow ventilation means for allowing frontal air to flow through the bottom section into an interior space, the at least pair of frame connectors being located behind the air-flow ventilation means to expose the air-flow ventilation means to frontal air flowing towards the goggle when on the wearer's face and the detachable shield is connected to the bottom section of the frame.

12. The goggle of claim 10 wherein the detachable shield is substantially flat when detached from the frame, the self-supporting material allowing the substantially flat shield to be bent for attachment so that the shield side sections curve back from the shield nose section which overlaps the central nose bridge when the shield connectors are inserted into the frame connectors.

13. A goggle comprising:
a lens;
a frame having a face contacting rim and a top section, side sections and a bottom section extending from the face contacting rim to a lens mounting section which supports the lens in spaced relation to a wearer's face, said frame including air-flow ventilation means located in the sections for venting the interior space to external air, a series of spaced connector receiving apertures formed in a bottom portion of the rim, a padding secured to substantially the entire periphery of the rim to cushion the frame against the wearer's face, said padding extending over the series of spaced connector receiving apertures in the bottom portion of the rim; and
a detachable shield formed by a self-supporting member having a series of snap-in connectors receivable within the series of spaced connector receiving apertures to detachably connect the shield to the bottom section of the frame with the padding preventing the snap-in connectors from contacting the wearer's face.

14. The goggle of claim 13 wherein at least the bottom section of the frame is formed of a resilient material, the snap-in connectors including a neck portion connecting an enlarged head to the self-supporting member, at least the enlarged head being formed of a rigid material of greater width than the diameter of the apertures to cause each aperture to expand as the enlarged head is urged into the aperture and then contract around the neck portion to thereby form a snap-in connector.

15. A goggle comprising:
a lens;
a frame having a top section, side sections and a bottom section which includes a central nose bridge for maintaining the lens in spaced relation to a wearer's face, the bottom section including a series of spaced connector receiving apertures formed adjacent the rear of the frame and air-flow ventilation means located in front of the connector receiving apertures for venting the goggle interior to exterior air, a detachable shield formed by a self-supporting member which is substantially flat and formed of a generally rigid material that allows a pair of shield side sections to be bent relative to a shield nose section, a series of snap-in connectors formed adjacent the edge of the pair of shield side sections and extending outward from the member, the shield being bent for attachment to the frame so that the shield nose section lies against the nose bridge and the series of snap-in connectors are detachably received in the series of connector receiving apertures to cause the shield side sections to curve rearwardly behind the air-flow ventilation means to allow frontal air to strike the shield side sections and be deflected upwardly through the air-flow ventilation means into the goggle interior.

16. The goggle of claim 15 wherein the series of snap-in connectors comprise a plurality of extending posts attached to the pair of shield side sections and extending upright therefrom, each post having an enlarged head to form with an associated aperture one of the snap-in connectors.

17. The goggle of claim 16 wherein the shield nose section has an extending portion which lies flat against the central nose bridge and does not carry any of the upright extending posts, whereby only the pair of shield side sections connect the shield to the goggle frame.

18. A goggle comprising:
a main lens;
an auxiliary lens having an extending tab;
a frame having a face contacting rim and a lens mounting section which supports the main lens in spaced relation to a wearer's face and defining a generally confined interior space, said frame including a bottom section extending between the rim and the lens mounting section and containing air-flow ventilation means for allowing frontal air to flow through the bottom section of the frame into the interior space;
a shield with a nose section and side sections extending therefrom for protecting a portion of the wearer's face which is not covered by the frame and lens;
means connecting said shield to said frame with a first portion of said shield sections being attached in the vicinity of the face contacting rim and behind the air-flow ventilation means in the bottom section to expose the air-flow ventilation means to frontal air flowing toward the goggle when on the wearer's face and a second portion of said shield sections being located in front of the lens mounting section to deflect some of the frontal air up over the exterior of the lens; and
said lens mounting section includes means spaced around the periphery thereof for detachably engaging the auxiliary lens with the tab extending downward and spaced in front of the first portion of the shield sections to create between the shield and the tab a space approximately equal to the width of the bottom section to allow easy grasping of the tab when the auxiliary lens is to be detached.

* * * * *